United States Patent [19]

Abraham et al.

[11] Patent Number: 4,704,402

[45] Date of Patent: Nov. 3, 1987

[54] METHOD OF TREATING SICKLE CELL ANEMIA

[75] Inventors: Donald J. Abraham, Murrysville, Pa.; Donald Witiak, Mt. Vernon, Ohio

[73] Assignee: University of Pittsburgh, Pittsburgh, Pa.

[21] Appl. No.: 553,957

[22] Filed: Nov. 21, 1983

Related U.S. Application Data

[63] Continuation of Ser. No. 390,704, Jun. 12, 1982, abandoned.

[51] Int. Cl.$^4$ .................. A61K 31/235; A61K 31/19
[52] U.S. Cl. .................................. 514/543; 514/571; 514/815
[58] Field of Search ............................. 424/317, 308

[56] References Cited

U.S. PATENT DOCUMENTS 3,262,850  7/1966  Jones et al. ........................... 167/65
4,062,974  12/1977  Coirault ................................ 424/308

OTHER PUBLICATIONS

Goodman et al.—the Pharmacological Basis or Therapeutics, 6th Ed, pp. 68, 91, 694.
AMA Drug Evaluations (4th Ed. 1980) pp. N-3-4-N-36.
National Library of Medicine, "Sickle Cell Anemia" Special Literature Search, Jan. 1970–Jun. 1974.
National Library of Medicine "Sickle Cell Anemia" Special Literature Search, Jul. 1974–Mar. 1978.
"Hemoglobin and the Sickling Cell" by Larry Varner Pitt Capsule, pp. 4–18.

*Primary Examiner*—Frederick E. Waddell
*Attorney, Agent, or Firm*—Arnold B. Silverman

[57] ABSTRACT

A method of treating a person for sickle cell anemia including administering to the person a therapeutically effective dosage of the compound

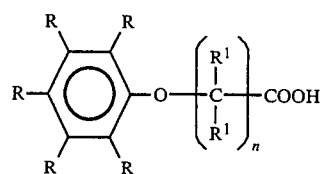

wherein at least one R=Cl, BR, $CH_3$ or $OCH_3$ and each other R=H, R'=H or $CH_3$ and n=1, 2, 3, 4 or 5. The compound is preferably selected from the group consisting of clofibrate, clofibric acid, p-chlorophenoxyacetic acid and phenoxyacetic acid. It is preferably administered in solid dosage form and may advantageously be employed in prophylactic treatment to resist sickle cell crises.

8 Claims, No Drawings

METHOD OF TREATING SICKLE CELL ANEMIA

This is a continuation of application Ser. No. 06/390,704, filed June 21, 1982, now abandoned.

BACKGROUND OF THE INVENTION

1. Field of the Invention

This invention relates to a method of treating persons for sickle cell anemia and, more specifically, relates to such a method which employs a specific group of compounds to resist the undesirable effects of the disease.

2. Description of the Prior Art

Sickle cell anemia is a hereditary blood disease which afflicts members of the Negro race and, to a very limited extent, Caucasians of Mediterranean and mideastern ancestry. The anemia results from the physical aggregation of the hemoglobin protein constituent in red blood cells. This aggregation results in a distortion in shape of deoxygenated red blood cells and causes impairment of flow of the blood through the capillaries (sickle cell "crises"). As the principal function of hemoglobin is to transport oxygen from the lungs to body tissues, efficient flow of oxygen throughout the body's tissues is impeded by the anemia due to a lower number of red blood cells. Sickle cell anemia also may have an indirect effect on the heart, lungs, kidneys, spleen, hips and brain. Sickle cell anemia crises can be extremely painful, can result in infections such as pneumonia, can result in skin ulceration, can contribute to strokes and seizures in the one afflicted and can also result in the development of chronic bone infections.

In general, the result of the difference between cells containing hemoglobin A, the normal hemoglobin, and hemoglobin S, the sickle cell hemoglobin, is that the former cell is generally flexible and bioconcave discoid in shape while the latter is more rigid and crescent shaped and typically has pointed ends. This rigidity and distortion in shape cause the cells to be lodged in the capillary. Hemoglobin molecules contain two beta polypeptide chains and two alpha polypeptide chains. In the sickle cell hemoglobin, a mutation is present in the beta chains. More specifically, the sixth amino acid of each beta chain is changed from glutamic acid to valine. As a result of this mutation, hemoglobin S upon deoxygenation polymerizes and causes the cell to assume the elongated, sickle-like configuration. As the sickle cells have a much shorter life span than normal red cells, the effect on the body is to deplete the total volume of blood cells thereby creating an anemic condition.

To the best of applicants' knowledge there has been no known effective means of arresting sickle cell anemia so as to prevent an individual who has this malady from experiencing one of the above-described problems. One known laboratory test employed in diagnosing sickle cell anemia is the performance of a hemoglobin electrophoresis test which is used to determine whether an individual has sickle cell anemia (homozygous) or merely the sickle cell trait (heterozygous), with the latter referring to an individual not having the disease but having the capability of transmitting the disease to offspring if mated to another heterozygote. Treatment for the various complications which have resulted from sickle cell anemia are known and should be distinguished from prophylactic activity (unknown) which would resist the occurrence of the complications. Currently, only symtomatic treatment is available. For example, people can treat the symptions by using analgesics for pain, and antibiotics for infection, but these approaches do not arrest the sickling phenomena.

There remains, therefore, a very real and substantial need for a method of minimizing the adverse consequences of sickle cell anemia through resisting sickle cell crises in an individual who has this abnormality.

SUMMARY OF THE INVENTION

The present invention has provided a method of employing a compound falling within a specific genus in treating sickle cell anemia patients. In a preferred embodiment, prophylactic doses, in solid dosage form, are administered to the patient in order to minimize the sickling effect.

It is an object of the present invention to provide a method of effectively resisting sickle cell crises and complications resulting from sickle cell anemia.

It is yet another object of the present invention to provide an effective yet easy-to-use method for treating sickle cell anemia.

It is a further object of the invention to provide a method of treatment which will permit victims of sickle cell anemia to live more normal lives.

These and other objects of the invention will be fully understood from the following description of the invention on reference to the illustrations appended hereto.

DESCRIPTION OF THE PREFERRED EMBODIMENT

In a preferred method of treatment of the present invention, a person having sickle cell anemia will be administered a therapeutically effective dosage of the compound

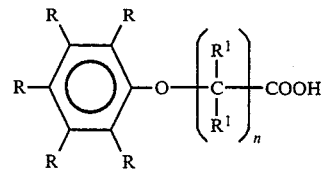

wherein at least one R=Cl, Br, CH$_3$ or OCH$_3$ and each other R=H, R'=H or CH$_3$ and n=1, 2, 3, 4 and 5. Where more than one R is selected from the group consisting of Cl, Br, CH$_3$ and OCH$_3$, (a) individual members of the group may be repeated or (b) combinations of the individual members or (c) both may be used. For example, methyl may be provided at two positions or methyl may be provided at one position and chlorine or bromine at another.

It is preferred that the compound be administered orally and in solid dosage form such as in a capsule, for example. The preferred dosage on a daily basis is about 1 to 5 gm/day depending upon the severity of the anemia and the weight of the patient.

With respect to the specifically preferred materials, it is preferred that the compound be selected from the group consisting of clofibrate, clofibric acid, p-chlorophenoxyacetic acid and phenoxyacetic acid.

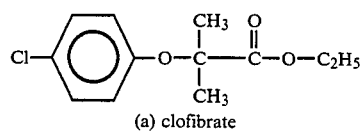

(a) clofibrate

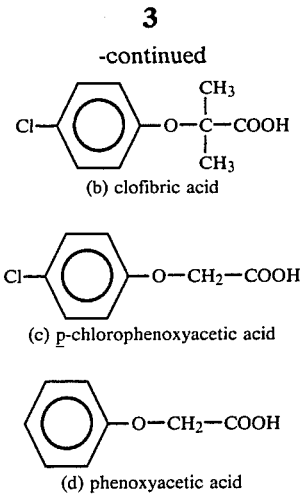

(b) clofibric acid (c) p-chlorophenoxyacetic acid (d) phenoxyacetic acid

The preferred species of compound are shown in these drawings.

As these compounds are known and the methods of making the same are known to those skilled in the art, there is no need to disclose such methods herein. For convenience of reference, however, it is noted that a method of making clofibrate and clofibric acid is disclosed in an article entitled "Preparation of [2-$^{14}$C]-2-(p-chlorophenoxy)-2-methylpropionic acid and its ethyl ester, [$^{14}$C] clofibrate", Journal of Labelled Compounds—Vol. XI, No. 2, pages 287-289 (1975).

The following method may be used to prepare p-chlorophenoxyacetic acid (c). To 2.00 g ($1.56 \times 10^{-2}$ mole) of p-chlorophenol is added 2.17 g ($1.56 \times 10^{-2}$ mole) of bromacetic acid. The vessel is placed under a $N_2$ atmosphere and 60 ml of dry THF (distilled from Na/benzophenone) is added along with 1.44 g NaH ($3.12 \times 10^{-2}$ mole, 50% oil dispersion) in portions. The reaction is heated at reflux over night. The following day the THF is removed in vacuo and to the residue is added 10 ml of water. The resulting solution is acidified with 37% HCl, extracted with water (2×20 ml), dried ($Na_2SO_4$) at concentrated in vacuo to give 2.30 g of a white solid, m.p. 153°-156° C. This is recrystallized from ether to give 1.73 g (m.p. 158°-159° C., yield 59%). The spectral data of the resultant product confirmed that of the literature contained in Aldrich Chemical Catalog, page 226, (1981-1982).

By repeating the previous process with phenol substituted for p-chlorophenol, phenoxyacetic acid is produced.

EXAMPLE

In order to confirm the effectiveness of these compounds in reducing the effect of hemoglobin aggregation, hemoglobin solubility tests were performed. The materials were tested according to the assay developed by Hofrichter et al. (J. Hofrichter, P. D. Ross and W. A. Eaton, Proc. Natl, Acad. Sci., USA, 73 30-35, 1976). This assay involves deoxygenation of concentrated sickle hemoglobin with dithionite in the presence of different concentrations of the drugs being tested. Samples are then sealed in quartz epr tubes under anaerobic conditions and spun at about 150,000×g for about 2½ hours at about 35° C. in an ultracentrifuge. This procedure pellets the polymerized HbS (sickle hemoglobin) to the bottom of the tubes and the supernatant (soluble HbS) is measured in the laboratory as the cyanmethemoglobin derivative. The more active the compound the greater the solubility of HbS and the smaller the pellet size. Activity is reported as a ratio of the HbS solubility with the particular drug to HbS solubility with no drug i.e. control. The higher the ratio the greater degree of activity of the drug.

The results of these tests are shown in table 1.

TABLE 1

| Drug Conc. | I | II | III |
|---|---|---|---|
| 5 mM | 1.018 | 1.044 | 1.017 |
| 10 mM | 1.064 | 1.077 | 1.009 |
| 20 mM | 1.155 | 1.162 | 1.047 |
| 40 mM | 1.302 | 1.276 | 1.097 |

The first column indicates the concentration of the particular drug. In the column headed I are the average ratios for the tests conducted with (b) clofibric acid. In the column headed II are the average results for the tests conducted with (c) p-chlorophenoxyacetic acid and column III contains the similar results for the drug (d) phenoxyacetic acid.

In order to evaluate the potential clinical significance of these molecules with respect to their antigelling results in vitro, it is possible to compare these assay results with the published solubility ratios and kinetic parameters (under these assay conditions) for correlation with clinical severity. See H. R. Sunshine, J. Hofrichter, W. A. Eaton, Nature, 275, 238 (1978). These authors report the solubility ratios which result from mixtures of HbS and fetal hemoglobin (HbF) or HbS and HbA. In the double heterozygous conditions of S/B+ thalassemia (15-30% HbA), which are clinically somewhat less severe than homozygous HbS disease, ratios of HbS/B+ thal to HbS/S range from 1.06 to 1.17. For conditions which are much less severe, as in the double heteroxygous condition of sickle/hereditary persistance of fetal hemoglobin (S/HPFH) in which red cells contain about 20 to 30% hemoglobin F, the solubility ratios obtained (HbS/HPFH) to HbS/S range from 1.19 to 1.26.

As will be appreciated from Table 1, the ratios needed for a clinically less severe condition (S/B+ thal to HbS/S e.g. 1.06-1.17) were reached with two of the three (I and II) compounds in the range of about 10 mM to 20 mM. As the concentration is increased, the ratio also increases. In these tests the average HbS concentration was around 3.7 mM. These results indicate that only about three or four moles of drug are needed for every mole of HbS in order to effect polymerization significantly. In red blood cells, the concentration of Hb is usually around 5 mM and with a typical hematocrit for homozygous S/S patients of 30%, the concentration of Hb in whole blood is approximately 1.5 mM.

It will be appreciated, therefore, that the method of this invention has provided a means for treating sickle cell anemia patients so as to resist undesired crises conditions resulting from the disease.

Whereas particular embodiments of the invention have been described above for purposes of illustration, it will be evident to those skilled in the art that numerous variations of the details may be made without departing from the invention as defined in the appended claims.

We claim:

1. A method of treating a person for sickle cell anemia comprising inhibiting HbS polymerization by administering to said person a therapeutically effective dosage of the compound

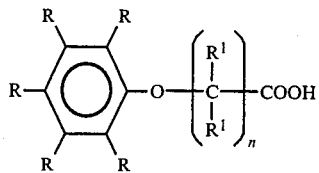

wherein at least one R=Cl, Br, CH$_3$ or OCH$_3$ and each other R=H, R'=H or Ch$_3$ and n=1, 2, 3, 4 or 5.

2. A method of treating a person for sickle cell anemia comprising administering to said person a therapeutically effective dosage of clofibrate or phenoxyacetic acid.

3. The method of claim 1 wherein said compound is selected from the group consisting of clofibric acid and p-chlorophenoxyacetic acid.

4. The method of claim 1 or 2 wherein said compound is administered orally.

5. The method of claim 4 wherein said compound is administered in solid dosage form.

6. The method of claim 5 wherein said compound is administered as a capsule.

7. The method of claim 5 wherein said compound is administered as a prophylactic to resist a sickle cell crisis in said person.

8. The method of claim 6 wherein said compound is given in a dosage of about 1 to 5 gm/day.

* * * * *